United States Patent [19]
Grabos, Jr. et al.

[11] Patent Number: 5,542,130
[45] Date of Patent: Aug. 6, 1996

[54] PROTECTIVE GOGGLE AND LENS WITH ADJUSTABLE VENTILATION

[75] Inventors: Fred F. Grabos, Jr.; George V. Dondero, both of Ketchum, Id.

[73] Assignee: Smith Sport Optics, Inc., Ketchum, Id.

[21] Appl. No.: 330,897

[22] Filed: Oct. 28, 1994

Related U.S. Application Data

[63] Continuation of Ser. No. 828,434, Jan. 30, 1992, Pat. No. 5,363,512.

[51] Int. Cl.$^6$ ........................................................ A61F 9/02
[52] U.S. Cl. ........................................................ 2/436; 2/441
[58] Field of Search ........................... 2/436, 437, 431, 2/426, 9, 10, 171.3, 8, 424, 425, 441, 443

[56] References Cited

U.S. PATENT DOCUMENTS

| | | |
|---|---|---|
| 1,588,775 | 6/1926 | Schumacher . |
| 2,537,275 | 1/1951 | Malcom, Jr. . |
| 3,395,406 | 8/1968 | Smith . |
| 3,444,561 | 5/1969 | Boyer . |
| 3,517,393 | 6/1970 | Beauchef . |
| 3,663,959 | 5/1972 | Loubeyre . |
| 3,718,937 | 3/1973 | Smith . |
| 3,945,044 | 3/1976 | McGee et al. . |
| 4,101,980 | 7/1978 | Stepan et al. ........................... 2/9 |
| 4,141,085 | 2/1979 | Adams, Sr. ........................ 2/436 X |
| 4,149,276 | 4/1979 | Castro . |
| 4,150,443 | 4/1979 | McNeilly . |
| 4,176,410 | 12/1979 | Matthias . |
| 4,179,756 | 12/1979 | Lucas . |
| 4,571,748 | 2/1986 | Carroll et al. . |
| 4,612,675 | 9/1986 | Broersma . |
| 4,649,577 | 3/1987 | Wiedner . |
| 4,698,856 | 10/1987 | Arai . |
| 4,785,481 | 11/1988 | Palmer, III et al. . |
| 4,868,929 | 9/1989 | Curcio . |
| 4,964,178 | 10/1990 | Giancarlo et al. . |
| 4,977,627 | 12/1990 | Metcalfe et al. . |
| 5,138,714 | 8/1992 | Smith . |

FOREIGN PATENT DOCUMENTS

| | | | |
|---|---|---|---|
| 1343531 | 10/1963 | France | ........................................ 2/436 |
| 150848 | 9/1981 | Germany . | |
| 562924 | 7/1944 | United Kingdom . | |
| 930735 | 7/1963 | United Kingdom . | |

OTHER PUBLICATIONS

Smith Dealer Catalog 1990–91, pp. 3 and 4 by Smith Sport Optics, Inc., Sun Valley, Idaho.

*Primary Examiner*—Peter Nerbun
*Attorney, Agent, or Firm*—Jenner & Block

[57] ABSTRACT

A ventilation adjustment assembly is provided for a goggle having a ventilated lens mounted in a frame. In one embodiment, the lens has one or more ventilation apertures forming a linear or curved path. An elongated shutter housing is formed by a base having pair of parallel sidewalls or spacers mounted on the lens on opposite sides of and in close proximity to the path of lens apertures. One or more apertures on the base align with the lens apertures. An elongated shutter is slidably disposed in the shutter housing. The shutter has one or more apertures which are alignable with apertures in the base and lens. By sliding the shutter within its housing, ventilation air flow is regulated as the shutter apertures move in and out of alignment with the base and lens apertures.

20 Claims, 3 Drawing Sheets

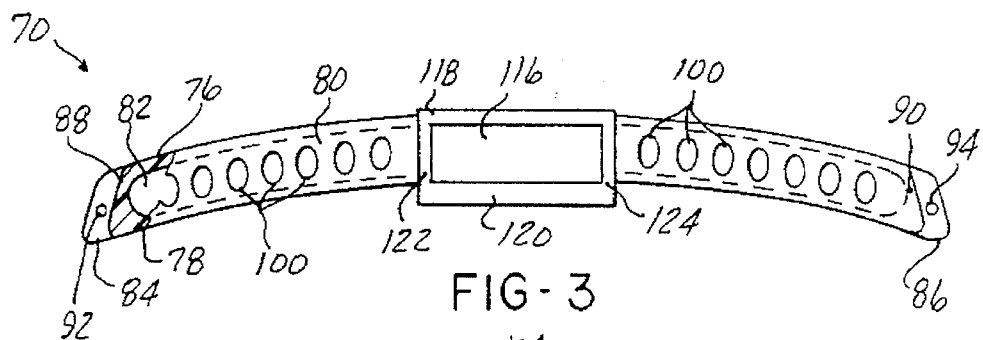
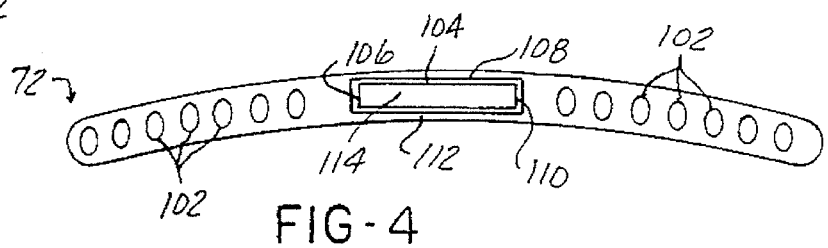
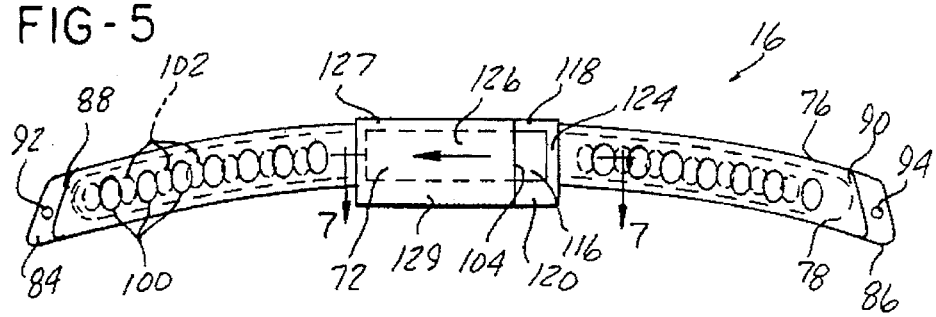
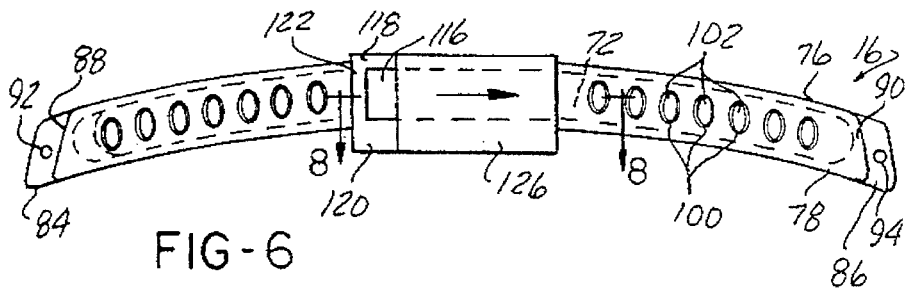
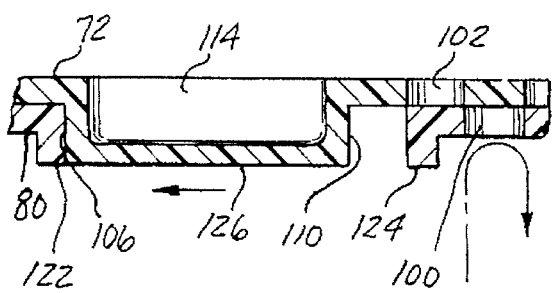
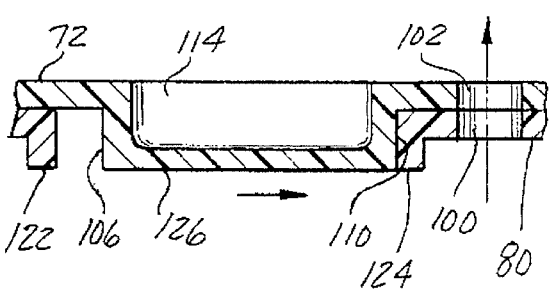

PROTECTIVE GOGGLE AND LENS WITH ADJUSTABLE VENTILATION

This is a continuation of application Ser. No. 07/828,434 filed Jan. 30, 1992, U.S. Pat. No. 5,363,512.

FIELD OF THE INVENTION

This invention relates generally to protective goggles having adjustable ventilation. More particularly, this invention relates to goggles which have a flexible lens housing and are particularly well-suited for use in skiing and other outdoor sports.

BACKGROUND OF THE INVENTION

Flexible goggles having a flexible housing in which a lens is mounted are well-known. Such goggles often use a thermal lens which includes two lenses spaced in parallel relation, such as by a closed cell foam spacer, to form an air-tight chamber between the two lenses for providing thermal insulation. Such goggles are commonly used by skiers and motorcyclists to protect their eyes from wind, precipitation and debris. They may also be used by surgeons and other medical personnel during operations and the like to protect eyes from fluids such as blood. The major drawback of conventional goggles is that condensation has a tendency to form on the inside of the lens thus fogging the lens and blocking the user's vision.

To prevent fogging, ski goggles have been provided with ventilating apertures which overcome the drawback of fogging, but which may, under some circumstances, allow excessive ventilation. This excessive ventilation results in a stream of cold air which may be unpleasant to the user, especially in extremely cold weather. Moreover, excessive ventilation can dry or otherwise damage sensitive tissue in and around the eyes. It has been proposed to control the passage of air by pivotable automatic flaps for closing an air passage opening when the user reaches a certain minimum speed. However, such devices are not practical, can be subject to icing of the closure mechanism, and are not manually adjustable by the user.

Ideally, a ventilation system for flexible goggles would be inexpensive to manufacture, manually adjustable and easy to operate. Ease of use is particularly important because users may often be wearing gloves or mittens which reduce their dexterity.

SUMMARY OF THE INVENTION

To overcome the deficiencies of the prior art, a goggle having adjustable ventilation is provided. In accordance with the invention, the goggle includes a frame in which a lens is mounted. The lens has one or more ventilation apertures. A ventilation adjustment assembly is mounted on the lens to regulate air flow through the ventilation aperture. The ventilation adjustment assembly uses a shutter or other suitable obstructing member which is movably disposed on the surface of the lens for being continuously positioned in and out of alignment with the lens' ventilation apertures.

In one embodiment, the lens has one or more ventilation apertures forming a linear or curved path. An elongated shutter housing is formed by a base having a pair of parallel sidewalls or spacers mounted on the lens on opposite sides of and in close proximity to the path of lens apertures. One or more apertures on the base align with the lens apertures. An elongated shutter is slidably disposed in the shutter housing. The shutter has one or more apertures which are alignable with apertures in the base and lens by sliding the shutter within its housing, ventilation air flow is regulated as the shutter apertures move in and out of alignment with the base and lens apertures. A strip of permeable foam is placed over the lens ventilation apertures to baffle ventilation air flow.

The present invention provides an adjustable ventilation system which can be inexpensively manufactured from just two plastic parts (the shutter and the shutter housing). In the embodiments disclosed herein, a simple sliding motion of the shutter allows easy manual adjustment of ventilation airflow over a continuous range. This feature makes the invention particularly useful in outdoor sports such as skiing.

Also, because goggle lenses are typically removable for easy replacement, the invention may be embodied on a lens by itself. This allows the lens assembly which includes the manually adjustable ventilation system to be sold separately and as a replacement part for conventional goggles. Thus, a user can convert a standard goggle with a replaceable single or thermal lens into a goggle system having manually adjustable ventilation by purchases of the lens assembly alone and replacement of the original lens.

BRIEF DESCRIPTION OF THE DRAWINGS

FIG. 3 is a front elevation view of the shutter housing shown in FIG. 2;

FIG. 4 is a top plan view of the elongated apertured shutter shown in FIG. 2;

FIG. 5 is a diagram showing the ventilation adjustment assembly shown in FIG. 1 with the shutter in a fully closed position;

FIG. 6 is a diagram showing the ventilation adjustment assembly shown in FIG. 1 with the shutter in a fully opened position;

FIG. 7 is a sectional view of the ventilation adjustment assembly taken along lines 7—7 in FIG. 5;

FIG. 8 is a sectional view of the ventilation adjustment assembly taken along lines 8—8 in FIG. 6.

DETAILED DESCRIPTION OF THE PREFERRED EMBODIMENTS

Figure 1:
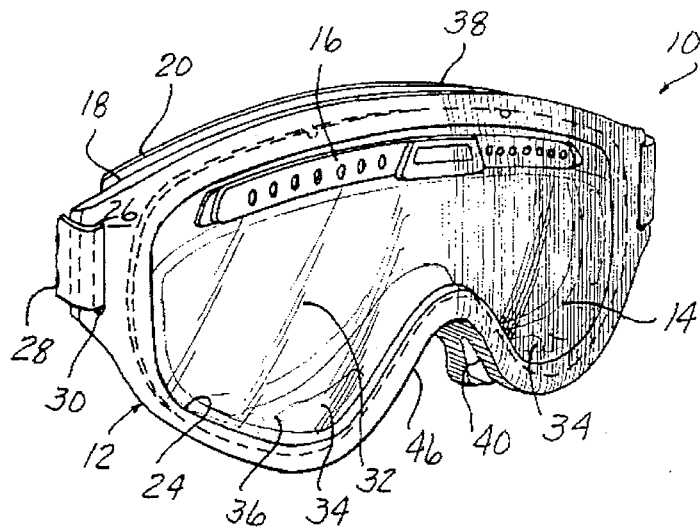
FIG. 1 is a perspective view of a goggle in accordance with the invention.

Turning now to the drawings in which similar reference characters denote similar elements throughout the several views, FIG. 1 is a perspective view of a goggle 10 in accordance with the invention. Goggle 10 generally comprises a frame 12, a lens structure 14 which is mounted in the frame 12, and a ventilation adjustment assembly 16 which is mounted on the lens structure 14.

Goggle frame 12 may have a generally annular structure and may be molded of one piece from a resilient flexible material such as a soft plastic or soft rubber. A face contacting flange or rim 18 is lined with a padding or cushion 20 of sponge-type material to seal frame 12 against the user's face (not illustrated). Lens structure 14 of flexible transparent material (which may be colored if desired) has a peripheral edge 22 which is received within a peripheral groove 24 formed interiorly around a front section 26 of frame 12. Lens structure 14 may be flat and bent to an arcuate configuration which fits frame 12, or may be curved and could, if desired, form a part of the structural support to maintain the shape of goggle 10.

To secure goggle 10 to the user's head, an elastic headband or strap 28 has folded, stitched ends which are received in slots 30 formed in frame front section 26. A slide buckle (not illustrated) allows adjustment of the length of elastic strap 28.

Goggle 10 is shaped to fit flush against the contours of the human face. Consequently, when worn by a user, a generally closed chamber 32 is located between lens structure 14 and the user's face (not illustrated). The user's body heat and evaporating perspiration cause moisture to condense inside chamber 32. Some of this condensation collects on the inside surface of lens structure 14 fogging lens structure 14 and thereby reducing the user's vision.

It is known that ventilation can reduce this problem. For example, goggle frame 12 may have a plurality of large vent openings 34 formed by ribs 36 which join the rim 18 to the front section 26. On the exterior side, the ribs 36 define with the rim 18 and front section 26 a channel 38 for a fibrous or open cell foam lining 40 which covers the openings 34 to allow a slow exchange of air between the goggle exterior and the closed chamber 32. While lining 40 is moisture and air permeable, it blocks snow and the like from entering chamber 32.

Other conventional ventilation systems, however, may be utilized in place of the illustrated vent apertures covered by a fibrous strip. While helpful, the ventilation provided by such systems is typically either insufficient to prevent fogging of lens structure 14 or so great as to cause the user discomfort. The goggle structure described above (excluding ventilation adjustment assembly 16) is well-known, and various modifications may be made thereto as desired.

Figure 2:
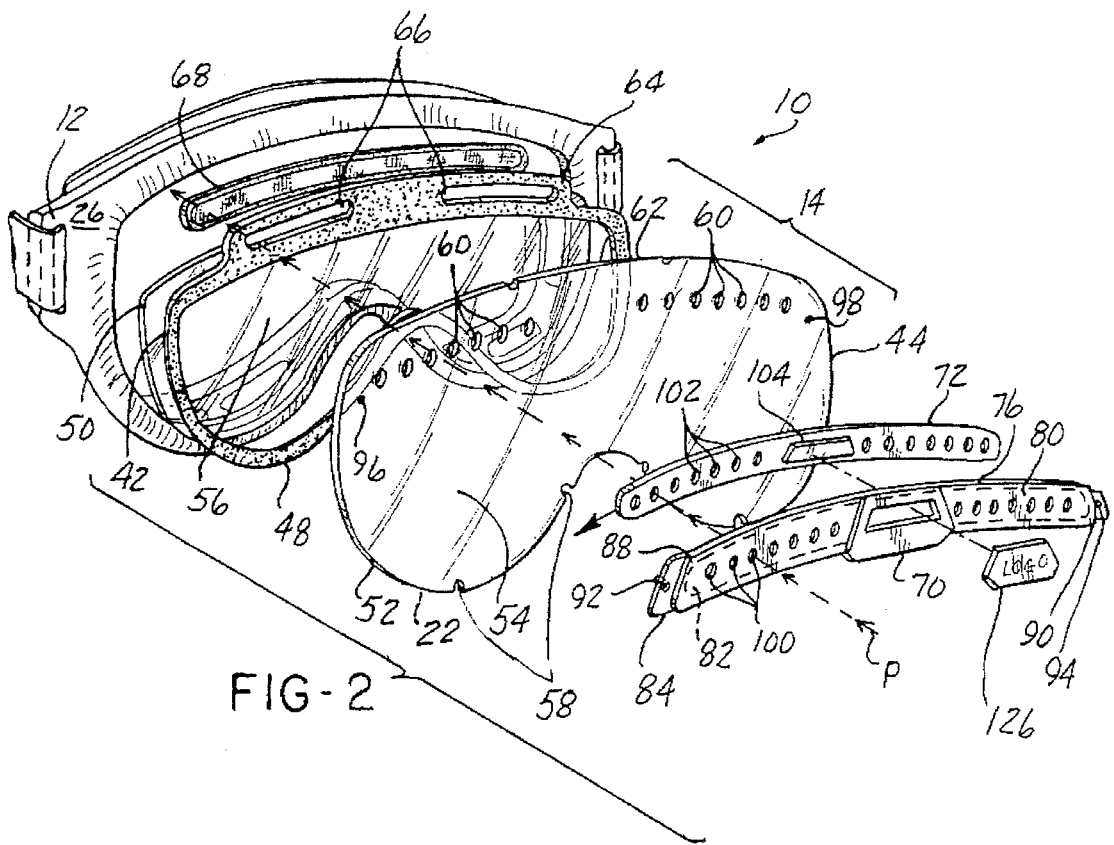
FIG. 2 is an exploded perspective view of the goggle shown in FIG. 1.

Referring to FIG. 2, lens structure 14 is illustrated in greater detail. In a preferred embodiment, the lens structure 14 is a so-called thermal lens, although the invention may be implemented with a single lens or other types of lenses. Lens structure 14 is formed of an inner lens 42 and an outer lens 44, both stamped from a generally planar sheet of transparent, semirigid plastic, the sheet being of uniform thickness. As best seen in FIG. 1, lenses 42 and 44 are horizontally elongated and intermediate their ends each is provided with a downwardly opening recess 46 to accommodate the nose of a wearer.

Lenses 42 and 44 are assembled and spaced in parallel relation by an interconnecting spacer 48. Interconnecting spacer 48 is made of closed cell, flexible foam which is bonded to lenses 42 and 44 in any suitable fashion so as to seal against both. Interconnecting spacer 48 is located in close proximity to peripheral edges 50 and 52 of lenses 42 and 44, respectively, and extends peripherally thereabout to define a central viewing area 54. Because interconnecting spacer 48 seals against both lenses 42 and 44, a space or chamber 56 between such lenses and central viewing area 54 is sealed to provide the thermal lens. It will be observed that lenses 42 and 44 can be integrally joined to define sealed space 56 between and inner and outer lens surfaces.

Lens structure 14 is deformed from the plane of the plastic sheets making up lenses 42 and 44 into a simple curve, as opposed to a compound curve. That is, for all horizontal sections taken through lens structure 14 at any point thereon, the curve will have essentially the same profile. Stated another way, the lens is curved only about its minor dimension and not about both minor and major dimensions.

Outer lens 44 is of a size and shape suitable for mounting lens structure 14 in front section 26. A plurality of keyholes 58 along periphery 52 of outer lens 44 engage corresponding fingers (not illustrated) in peripheral grove 24 of frame front section 26 to releasably secure outer lens 44 therein.

In accordance with the invention, outer lens 44 also has a plurality of evenly spaced apertures 60 for ventilating chamber 32. Apertures 60 may be of uniform size, spacing and circular shape and the distance between each of apertures 60 exceeds their individual width or diameter. The invention may also be practiced using apertures of irregular size, shape and spacing, or using only a single aperture. Apertures 60 are generally in linear alignment, although they may define a path that is somewhat curved about an axis running perpendicular to the plane of outer lens 44. Apertures 60 are arranged in a horizontal orientation near top edge 62 of outer lens 44. Apertures 60 need not be provided near the middle portion of outer lens 44.

Foam spacer 48 and inner lens 42 are somewhat shorter than outer lens 44, so that apertures 60 are outside the area encircled by foam spacer 48 and are, therefore, not obstructed by inner lens 42. It will be observed that this construction permits the use of ventilation apertures in a thermal lens without puncturing sealed space 56. An elongated tab 64 also constructed of closed cell foam extends upwardly from spacer 48 and is mounted to the region of outer lens 44 containing the plurality of apertures 60. Two slotted apertures 66 in elongated tab 64 are positioned behind apertures 60 to permit the movement of ventilation air therethrough.

An elongated open cell foam filter 68 is horizontally orientated and is mounted on and in alignment with tab 64. Open cell foam filter 68 serves to filter air streaming through ventilation apertures 60 and slotted apertures 66, thereby preventing the intrusion into chamber 32 of particles or droplets of precipitation such as rain or snow, for example. Open cell foam filter 68 also serves to baffle ventilation air flow having an otherwise excessive velocity.

As best seen in FIGS. 1 and 2, ventilation adjustment assembly 16 is located over the plurality of apertures 60 on outer lens 44 to regulate the flow of air therethrough. It will be noted that ventilation adjustment assembly 16 is mounted near the periphery of central viewing area 54 so as to minimize interference with the user's vision. Ventilation adjustment assembly 16 comprises a three-sided shutter housing or slide 70 in which an elongated shutter 72 is slidably disposed. As discussed below in greater detail, shutter housing 70 is mounted on lens 44 over apertures 60 to create a channel thereover. A thin, elongated apertured shutter 72 or other suitable obstruction member is slidably disposed in this channel, and various positions of the shutter 72 allow more or less ventilating air to pass through lens apertures 60. Shutter housing 70 and shutter 72 may be slightly arcuate to accommodate the curvatures of lens 44 and the path of alignment of apertures 60.

Referring to FIGS. 2 and 3, the shutter housing 70 has a three-sided cross-section formed by a pair of thin, parallel spacers or sidewalls 76 and 78 mounted on lens 44 and a relatively wider cover 80 which is mounted onto the sidewalls 76 and 78. Sidewalls 76 and 78 are positioned on opposite sides of the line of apertures 60 in lens 44. Lens 44, sidewalls 76 and 78, and cover 80 define a channel or track 82 extending over the apertures 60 along the width of outer lens 44. Flanges 84 and 86 are attached to opposite longitudinal ends 88 and 90, respectively, of shutter housing cover 80 for mounting cover 80 to the lens 44. Index posts or fingers 92 and 94 extend outwardly from flanges 84 and 86, respectively, and are received by index apertures 97 and 98 in lens 44. Sidewalls 76 and 78 and flanges 84 and 86 are mounted to lens 44 by solvent bonding.

Shutter housing cover 80 has a plurality of apertures 100 of substantially the same number, size and spacing as the apertures on lens 44. Shutter housing 70 is mounted so that apertures 100 on cover 80 are substantially in alignment with apertures 60 on lens 44. Apertures 100 may have an oval shape with their respective elongated axes generally perpendicular to the elongated length of shutter housing 70. Goggle 10 could be constructed (not shown) without shutter housing cover 80 using only sidewalls 76 and 78 to form a channel, such as channel 82, as long as sidewalls 76 and 78 would not cover apertures 102 of shutter 72 to an undesirable degree.

As best seen in FIG. 2, a ventilation path for air flow extends along path P through apertures 100 on shutter housing cover 80, apertures 60 on lens 44, slotted apertures 66 on elongated tab 64 and the open cell foam filter 68. It will be observed that a person wearing goggle 10 tends to face his or her direction of travel, as is typical. Because a person wearing goggle 10 can travel at a relatively high rate of speed through cold winter air, such as with skiing or snowmobiling, cold air can be forced through path P and into chamber 32 at a velocity to cause the person some discomfort. Therefore, it is desirable to regulate the flow of air through apertures 100, as well as to control the amount of airflow for different fogging conditions which will depend on atmospheric conditions.

In accordance with the present invention, regulation of ventilation air flow along path P is provided by elongated shutter 72 which is slidably disposed inside of channel 82 of shutter housing 70. Shutter 72 is curved to follow the path of alignment of apertures 60 on outer lens 44 and the contours of channel 82. A plurality of apertures 102 are spaced along the elongated length of shutter 72. The apertures 102 are substantially identical in size, shape, and spacing to the apertures 100 on shutter housing cover 80, but may also be slightly smaller in size or fewer in number.

FIGS. 5 and 6 show an assembled ventilation adjustment assembly in closed and open positions, respectively. As illustrated by the arrows, shutter 72 may be slidably positioned to bring apertures 102 on shutter 72 in and out of alignment with apertures 100 on shutter housing cover 80. When shutter apertures 102 are completely aligned with shutter housing cover apertures 100 (as shown in FIG. 6) apertures 100 are unobstructed, and ventilation air flows freely along path P (see FIG. 2). As shutter apertures 102 are moved out of alignment with shutter housing cover apertures 100, air flow through apertures 100 is progressively obstructed. When shutter apertures 102 are completely out of alignment with apertures 100 (as shown in FIG. 5), apertures 100 are completely obstructed, and no ventilation air flows along path P. It will be noted that the spaces between each of apertures 100 (and apertures 102) must be at least as wide as the apertures themselves. In this manner, the portions between apertures 102 of shutter 72 will be sufficiently wide to completely block apertures 100.

Referring to FIG. 4, elongated shutter 72 has a raised region 104 located at the midsection of shutter 72. Raised region 104 comprises four raised edges 106, 108, 110 and 112 which circumscribe a rectangular void 114. Rectangular void 114 serves to reduce the cost of manufacturing shutter 72 by eliminating the plastic or like material which would otherwise fill void 114. Alternatively, raised region 104 may be solid.

As best seen in FIGS. 2–3, shutter 72 is disposed in channel 82 so that raised area 104 projects outwardly through an aperture or collar 116 in shutter housing cover 80. Aperture 116 is generally rectangular in shape and is circumscribed by braces 118 and 120 and stops 122 and 124. Braces 118 and 120 are superimposed on sidewalls 76 and 78, respectively. Braces 118 and 120 may be slightly thicker and wider than sidewalls 76 and 78, and serve to strengthen shutter housing cover 80 along the length of aperture 116. Without the braces 118 and 120, shutter housing cover 80 tends to buckle at a point along aperture 116 when flexible frame 12 is bent.

Stops 122 and 124 are slightly thicker than shutter housing cover 80, and serve to define the range within which shutter 72 is slidable, as discussed below. Raised region 104 should protrude slightly past braces 118 and 120 and stops 122 and 124. A generally rectangular plate 126 (shown in FIGS. 2, 5 and 6) is mounted flat onto raised region 104. Rectangular plate 126 serves as a manual adjustment button or knob by which the user's finger can engage shutter 72 for sliding motion within channel 82. Plate 126 is larger in area than raised area 104 and may have longitudinal edges 127 and 129 which overhang braces 118 and 120, respectively, as shown in FIG. 5. The surface of plate 126 has ridges (not illustrated) which can be shaped into raised letters of a trade name or logo. These ridges provide the user's finger with a better gripping surface when engaging plate 126.

Referring to FIGS. 5–8, the operation of ventilation adjustment assembly 16 may be more thoroughly understood. For clarity, FIGS. 5 and 6 depict an assembled ventilation adjustment assembly. Consequently, plate 126 is positioned over raised area 104, which is therefore not shown. It should be understood that while plate 126 and aperture 116 and void 114 are depicted as plain rectangles in FIGS. 3–6, in practice, aesthetic considerations might dictate the use of more stylized designs, such as depicted in FIG. 2, and that the invention fully contemplates the use of such alternative designs.

Shutter 72 fits snugly in channel 82. In this manner (and particularly when shutter housing 70 and shutter 72 are curved), the sides of shutter 72 will impinge the interior walls of channel 82. This contact creates a friction force which tends to restrain movement of shutter 72 and keep shutter 72 in a fixed position within channel 82 until the wearer physically changes the position of shutter 72 as hereinafter described.

When the user's finger engages plate 126 and applies a force in a direction parallel to the surface of plate 126 which is sufficient to overcome the frictional resistance, shutter 72 is slidably moved in that direction in channel 82 to open, partially close, or close apertures 60. It will be observed that braces 118 and 120 of shutter housing cover 80 slidably engage with edges 108 and 112, respectively, of raised region 104, as the user slides plate 126 and shutter 72 back and forth.

As shown in FIGS. 7 and 8, front plate 126 is integrally connected to shutter 72 by edges 106 and 110 of raised region 104. Referring to FIGS. 5 and 7, a user may, by engaging front plate 126, slide shutter 72 toward end 88 of shutter housing cover 80 until edge 106 of raised region 104 abuts stop 122. Likewise, as shown in FIGS. 6 and 8, shutter 72 may be slid toward end 90 of shutter housing cover 80 until edge 110 of raised region 104 abuts stops 124. In this manner, the spacing between backstop 122 and 124 determines the range of lateral movement of shutter 72. Stops 122 and 124 are spaced sufficiently apart to allow shutter 72 a range of movement greater than the width of apertures 100, but less than the distance between each of apertures 100. This range is just sufficient to allow movement of shutter 72 from the fully closed position of FIG. 5 to the fully open position of FIG. 6.

Apertures 102 are then positioned on shutter 72 so that when shutter 72 is at one extreme of its range of sliding movement, shutter apertures 102 are substantially in alignment with shutter housing cover apertures 100. When shutter 72 is positioned at the opposite extreme of its range of sliding movement, shutter apertures 102 should be completely out of alignment with shutter housing cover apertures 100. Shutter 72 may also be placed at intermediate positions on its range of sliding movement to place shutter apertures 102 in partial alignment with shutter housing cover apertures 100.

For example, in FIGS. 5 and 7, shutter 72 has been slid toward shutter housing cover end 88 until edge 106 abuts stop 122. In this position, each shutter aperture 102, such as aperture 102 in FIG. 7 is out of alignment with its corresponding shutter housing cover aperture 100. In FIG. 7, aperture 100 is completely blocked, and no ventilation air flows through aperture 100 or any other apertures 100, which are all similarly blocked.

In comparison, as seen in FIGS. 6 and 8, shutter 72 has been slid toward shutter housing cover end 90 until edge 110 of raised region 104 abuts stop 124. In this position, each shutter hole 102 is in complete alignment with its corresponding shutter housing cover hole 100. Thus, each shutter housing cover hole 100 is unobstructed by shutter 72, and ventilation air flows freely through apertures 100 each of which is also unobstructed.

In addition, the shutter 72 may be left in some intermediate position, thereby providing a continuous range of adjustability for ventilation air flow through apertures 100 and into chamber 32. In this manner, a user may manually engage plate 126 to position shutter 72 so that the precisely desired level of ventilation is received into chamber 32.

Various changes can be made to the illustrated embodiments. For example, lens 44 could have only one ventilation hole (as opposed to a plurality). Lens ventilation apertures 60 could be vertically oriented. Ventilation apertures of different or irregular shape, size, and spacing could be used in lens 44, so long as the apertures in shutter housing cover 80 and shutter 72 are alignable therewith. Shutter housing 70 can be replaced by other suitable devices for slidably mounting shutter 72 on lens 44, including grooves in the lens itself for slidably receiving shutter 72. Alternatively, shutter 72 can be mounted between portions of inner lens 42 and outer lens 44 which extend beyond the perimeter of foam spacer 48. Additionally, shutter 72 can be adapted for discrete (as opposed to continuous) movement in channel 82, such as by using detents or the like. Shutter housing cover 80 could be replaced by a plurality of cross members (not illustrated) spanning parallel sidewalls 76 and 78 to capture sliding shutter 72 therebetween. Shutter 72 may also be of any suitable shape and may be mounted for rotating (or opposed to slidable) movement relative to the surface of lens structure 14. Shutter 72 need not be in direct contact with the lens surface, and could, for example, be mounted in spaced relation to the lens surface.

As indicated above, lens structure 14 is removable from goggle 10 for easy replacement. Consequently, the lens structure 14 which includes ventilation adjustment assembly 16 may be sold separately and as a replacement part for conventional goggles. A user may convert a standard goggle with a replaceable single or thermal lens into a goggle such as goggle 10 having adjustable ventilation by purchasing lens structure 14 along and replacing the user's original lens.

Figure 9:
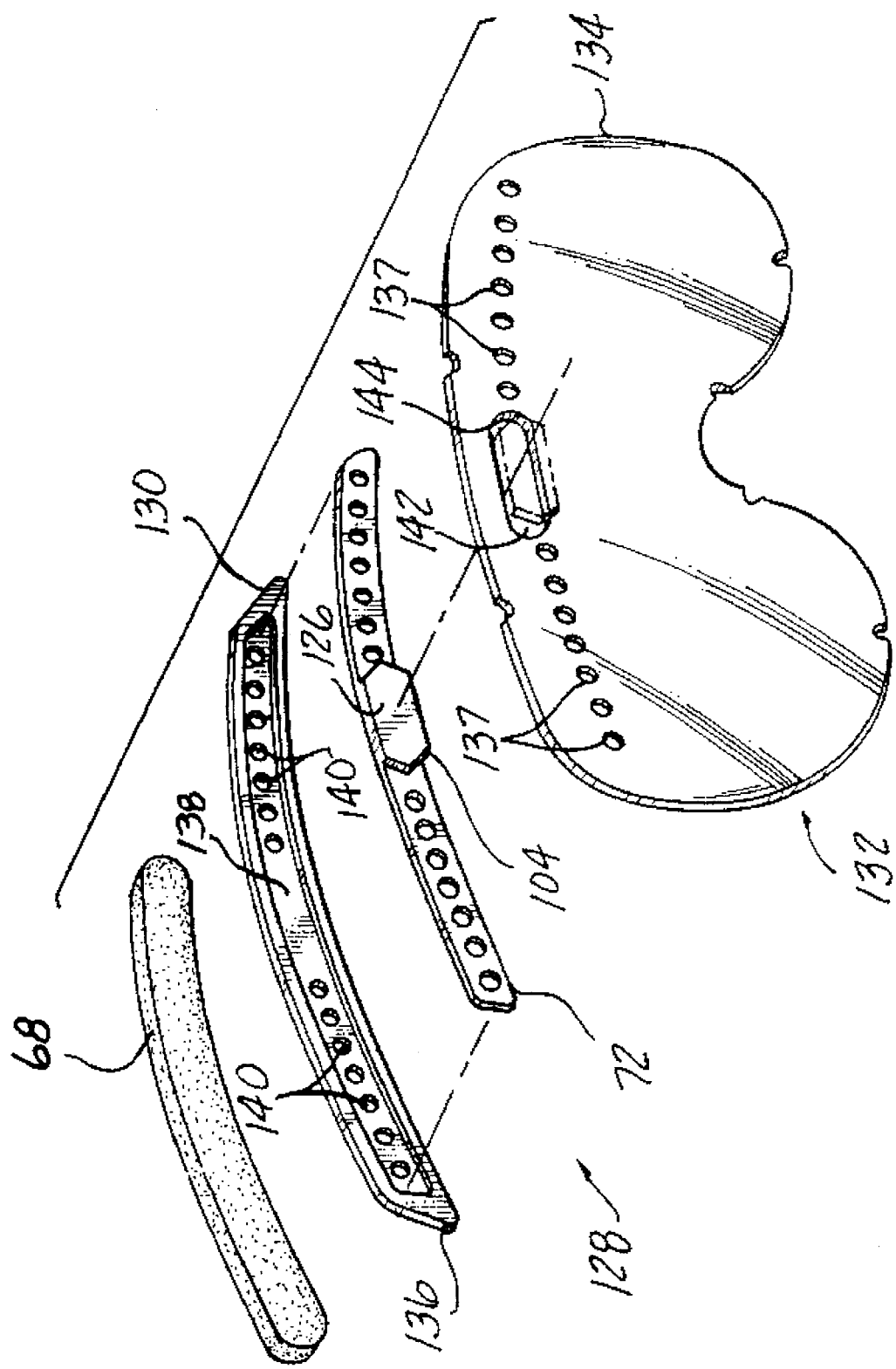
FIG. 9 is a partial exploded view of a goggle in accordance with a second embodiment of the invention.

Referring to FIG. 9, an exploded view of a goggle 128 employing a second embodiment of the invention is provided. Goggle 128 is similar to the goggle 10 described above, and those parts of goggle 128 that differ from goggle 10 are illustrated in FIG. 9. Goggle 128 includes a ventilation adjustment assembly 130 mounted on a lens structure 132. Lens structure 132 is substantially identical to lens structure 14, and includes an outer lens 134 having a plurality of evenly spaced ventilation apertures 137. (For clarity, while a number of ventilation apertures 137 are shown, only four are indicated by a reference numeral.)

Ventilation air flow through apertures 137 is regulated by ventilation adjustment assembly 130. In goggle 128, the ventilation adjustment assembly 130 is mounted on the inside surface (i.e., that surface of the lens structure which faces a person wearing goggles 10) of the outer lens 134, as best seen in FIG. 9. Mounting the ventilation adjustment assembly 130 on the inside surface of lens structure 132 subjects housing 136 to certain compression (as opposed to tension) forces when goggle 10 is bent or flexed. It has been found that housing 136 more easily withstands these compression forces. Ventilation adjustment assembly 130 includes a three-sided shutter housing 136 which is mounted behind outer lens 134 over apertures 137. Shutter housing 136 includes a shutter housing cover 138 having a plurality of ventilation apertures 140. The elongated open cell foam filter 68 may be mounted over apertures 140 to filter air'streaming therethrough. Because shutter housing 136 resides behind outer lens 134, it occupies the space which, in goggle 10, is occupied by tab 64. Therefore, goggle 128 need not includes a tab such as tab 64.

The thin, elongated shutter 72, described above in connection with goggle 10, is disposed in shutter housing 136 in the manner described above in connection with shutter housing 70. Raised area 104 of shutter 72 is disposed behind outer lens 134 so that raised area 104 projects outwardly through an aperture 142 in outer lens 134. Aperture 142 performs the same function as aperture 116 of shutter housing cover 80. The periphery 144 of aperture 142 corresponds in function to the braces 118 and 120 and stops 122 and 124 of shutter housing cover 80. Front plate 126 is integrally connected to shutter 72 as described above, to serve as a button or knob by which the user's finger can engage shutter 72 for sliding motion within shutter housing 136.

It will be observed that while shutter housing 136 is mounted on the inside surface of outer lens 134, the orientation of shutter 72 is the same in both goggle 10 and goggle 128. Consequently, shutter housing 136 has no central aperture, such as aperture 116, for receiving raised area 104 of shutter 72. Instead, raised area 104 projects through aperture 142 in outer lens 134.

Other modifications which can be made within the scope of the present invention will be understood in view of the foregoing. It is desired not to limit the invention to the embodiments illustrated as it will be apparent that a number of modifications can be made therein.

I claim:

1. A goggle having adjustable ventilation, comprising:

a frame having an annular structure defining a viewing area and a lens mounting means;

a lens mounted in said frame and having a first plurality of ventilation apertures formed through the lens;

a member having a second plurality of ventilation apertures formed through the member; and adjustment means for movably mounting the member with respect to the lens to move the first and second plurality of ventilation apertures in and out of alignment to provide adjustable ventilation through the lens.

2. The goggles of claim 1 wherein the adjustment means provides a continuous range of adjustability to progressively adjust alignment of the first and second plurality of ventilation apertures.

3. The goggle of claim 2 including stop means positioned on the lens to abut the member when the first and second plurality of apertures are completely out of alignment so as to completely block any ventilation through the lens.

4. The goggle of claim 1 including a projection extending from one of the member or adjustment means for manual engagement to adjust the alignment between the first and second plurality of ventilation apertures.

5. The goggles of claim 1 wherein the lens has a central viewing area, and the first plurality of ventilation apertures are spaced from the central viewing area and are located near a periphery of the lens.

6. The goggle of claim 5 wherein the first plurality of ventilation apertures are arranged in a generally horizontal orientation near a top edge of the lens when the frame is worn by a user.

7. The goggle of claim 5 wherein a third plurality of ventilation apertures are formed through the lens and located near the periphery of the lens, the first plurality of ventilation apertures being located on one side of a wearer's nose and the third plurality of ventilation apertures being located on an opposite side of the wearer's nose when the goggle is worn, an additional member having a fourth plurality of ventilation apertures formed through the additional member, and further adjustment means movably mounting the additional member with respect to the lens to move the third and fourth plurality of ventilation apertures in and out of alignment to provide additional adjustable ventilation through the lens.

8. The goggle of claim 7 wherein the adjustment means includes a master control device linked to both the first named member and the additional member for moving both members at the same time.

9. The goggle of claim 1 wherein at least certain of the second plurality of ventilation apertures are substantially identical in size, shape and spacing to at least certain of the first plurality of ventilation apertures, and the adjustment means allows at least some of the first and second ventilation apertures which are substantially identical in size, shape and spacing to coincide.

10. The goggle of claim 1 wherein the member comprises a shutter which is slidably movable to selectively obstruct the alignment of the first and second plurality of ventilation apertures.

11. The goggle of claim 10 wherein the shutter is sized to snugly move with a friction fit to thereby maintain the shutter in a fixed position after adjustment.

12. The goggle of claim 1 wherein the lens mounting means includes a peripheral groove located in the annular structure, and the lens includes a peripheral edge which is releasably engagable with the peripheral groove to allow replacement of the lens.

13. The goggle of claim 12 wherein the frame is formed from a resilient flexible material with the peripheral groove being formed interiorly around the annular structure, and the lens which is releasably engagable therewith is formed of a semirigid material.

14. The goggle of claim 1 wherein the frame includes a plurality of vent openings to provide additional ventilation to the interior space behind the lens whereby the goggle provides the combination of non-adjustable ventilation through the frame and adjustable ventilation through the lens.

15. The goggle of claim 14 wherein at least one of the plurality of ventilation apertures and the plurality of vent openings have an air permeable filter which covers the same.

16. A goggle having adjustable ventilation, comprising:

a frame having an annular structure with a lens mounting section defining an interior space, a plurality of frame ventilation apertures formed in the annular structure to allow air-flow ventilation through the frame and into the interior space;

a lens mounted in said lens mounting section and having a plurality of lens ventilation apertures formed through the lens and located near a periphery of the lens to allow air-flow ventilation through the periphery of the lens and into the interior space;

a slidable shutter having a plurality of shutter ventilation apertures formed through the slidable shutter;

continuous adjustment means for slidably mounting the shutter adjacent the plurality of lens ventilation apertures to progressively superimpose the shutter and lens ventilation apertures in and out of alignment to thereby provide a continuous range of air-flow ventilation into the interior space through the lens and in supplement to the air-flow ventilation through the frame.

17. The goggle of claim 16 wherein the plurality of lens ventilation apertures are spaced to form an elongated path near the periphery of the lens, the slidable shutter being elongated with at least some of the shutter ventilation apertures being spaced to be superimposed over the lens ventilation apertures, and the continuous adjustment means snugly receives the elongated slidable shutter to provide a friction fit to maintain the elongated shutter in a stationary position after slidable movement to thereby maintain a fixed amount of air-flow ventilation within the continuous range.

18. The goggle of claim 17 including an elongated air permeable filter, and mounting means attached to the lens for locating the elongated air permeable filter near the periphery of the lens to coincide with the shutter and lens ventilation apertures when aligned with each other.

19. The goggle of claim 17 wherein the continuous adjustment means includes a manual adjustment member projecting from the slidable shutter and manually slidable along the elongated path to different stationary positions to thereby manually adjust the amounts of air-flow ventilation through the lens within the continuous range.

20. The goggle of claim 16 wherein the annular structure of the frame is formed from a resilient flexible material, the lens mounting section including a peripheral groove formed interiorly around the annular structure, the lens is formed of a semirigid material which supports the slidable shutter and the continuous adjustment means, the lens further having a peripheral edge which is releasably engagable with the peripheral groove of the frame to allow replacement of the lens and attached slidable shutter and continuous adjustment means.

* * * * *